United States Patent [19]
Laborie et al.

[11] Patent Number: 5,474,056
[45] Date of Patent: Dec. 12, 1995

[54] SUSPENSION AND RETRACTION SYSTEM FOR ENDOSCOPIC SURGERY AND METHOD FOR USING SAME

[75] Inventors: Raymond G. Laborie, St. Bruno; Yves M. Dion, St. Augustin, both of Canada

[73] Assignee: Laborie Enterprises Inc., Quebec, Canada

[21] Appl. No.: 197,602

[22] Filed: Feb. 17, 1994

Related U.S. Application Data

[63] Continuation-in-part of Ser. No. 761,375, Sep. 18, 1991, abandoned.

[51] Int. Cl.⁶ .................................................. A61B 17/02
[52] U.S. Cl. ........................ 600/214; 606/198; 600/204; 600/236
[58] Field of Search .............................. 128/20, DIG. 26, 128/877, 878, 882, 845, 4, 897, 898; 602/32, 33, 34, 35, 40; 606/198, 191, 185, 130, 201; 604/107

[56] References Cited

U.S. PATENT DOCUMENTS

| | | |
|---|---|---|
| 2,202,748 | 5/1940 | Solo . |
| 3,585,578 | 1/1975 | Milo . |
| 3,823,709 | 7/1974 | McGuire . |
| 4,099,521 | 7/1978 | Nestor et al. . |
| 4,457,300 | 7/1987 | Budde . |
| 4,573,452 | 3/1986 | Greenburg . |
| 4,593,681 | 6/1986 | Soni . |
| 4,608,965 | 9/1986 | Anspach, Jr. . |
| 4,621,625 | 11/1986 | Powlan . |
| 4,622,955 | 11/1986 | Fakhrai . |
| 4,632,458 | 12/1986 | Brown et al. . |
| 4,654,028 | 3/1987 | Suma . |
| 4,690,674 | 9/1987 | Dalglish . |
| 4,809,687 | 3/1989 | Allen . |
| 4,850,563 | 7/1989 | Grout . |
| 4,867,404 | 9/1989 | Harrington et al. . |
| 4,909,789 | 3/1990 | Taguchi et al. . |
| 4,926,849 | 5/1990 | Downey . |
| 4,932,395 | 6/1990 | Mehdizadeh . |
| 4,945,896 | 8/1990 | Gade . |
| 5,003,967 | 4/1991 | McConnell . |
| 5,065,739 | 11/1991 | Forrest et al. . |
| 5,318,012 | 6/1994 | Wilk ........................................... 128/20 |
| 5,372,147 | 12/1994 | Lathrop, Jr. et al. ................. 128/20 X |

FOREIGN PATENT DOCUMENTS

| | | |
|---|---|---|
| 736949 | 5/1980 | U.S.S.R. . |
| 1360708 | 12/1987 | U.S.S.R. . |

OTHER PUBLICATIONS

Izmailov, et al., "Universal Retractor For Cavity Surgery", Biomed. Eng., Sep.–Oct. 1974, pp. 320.

Primary Examiner—Richard J. Apley
Assistant Examiner—Beverly M. Flanagan
Attorney, Agent, or Firm—Sherman and Shalloway

[57] ABSTRACT

A method for endoscopic surgery utilizes a wire or wires to support the anterior wall of a body cavity. The method may include the utilization of a retractor specifically designed for endoscopic surgery.

1 Claim, 11 Drawing Sheets

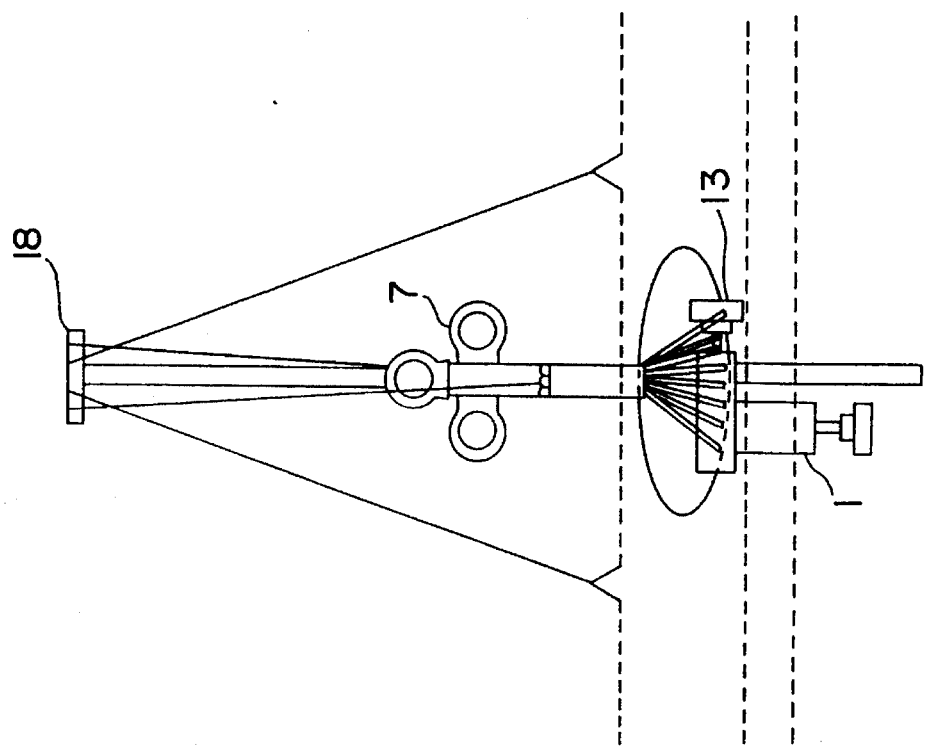
FIG. IB
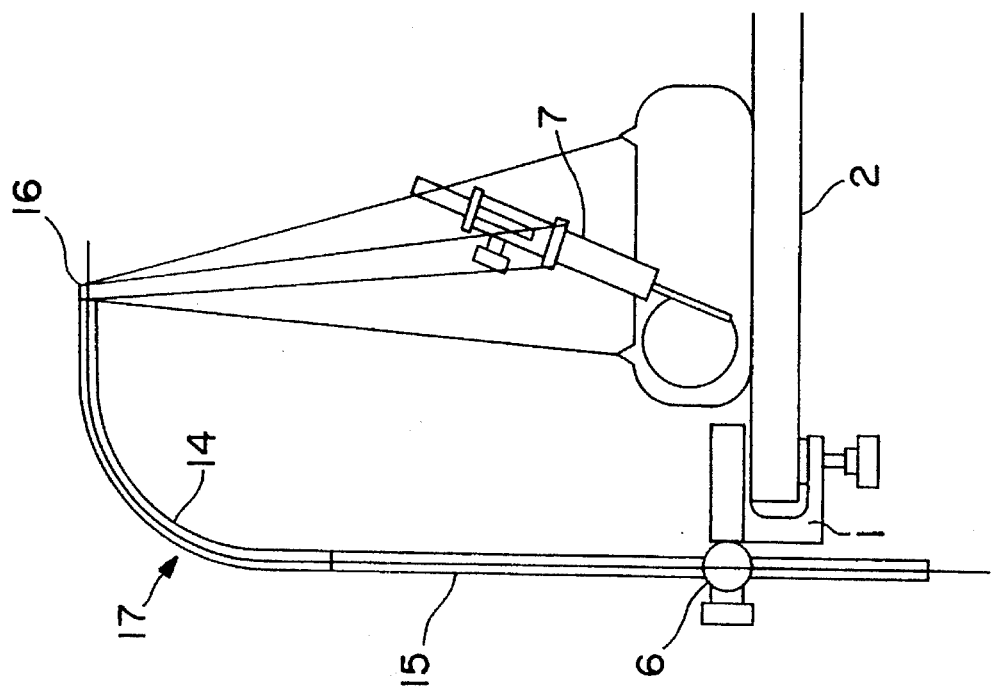
FIG. IA

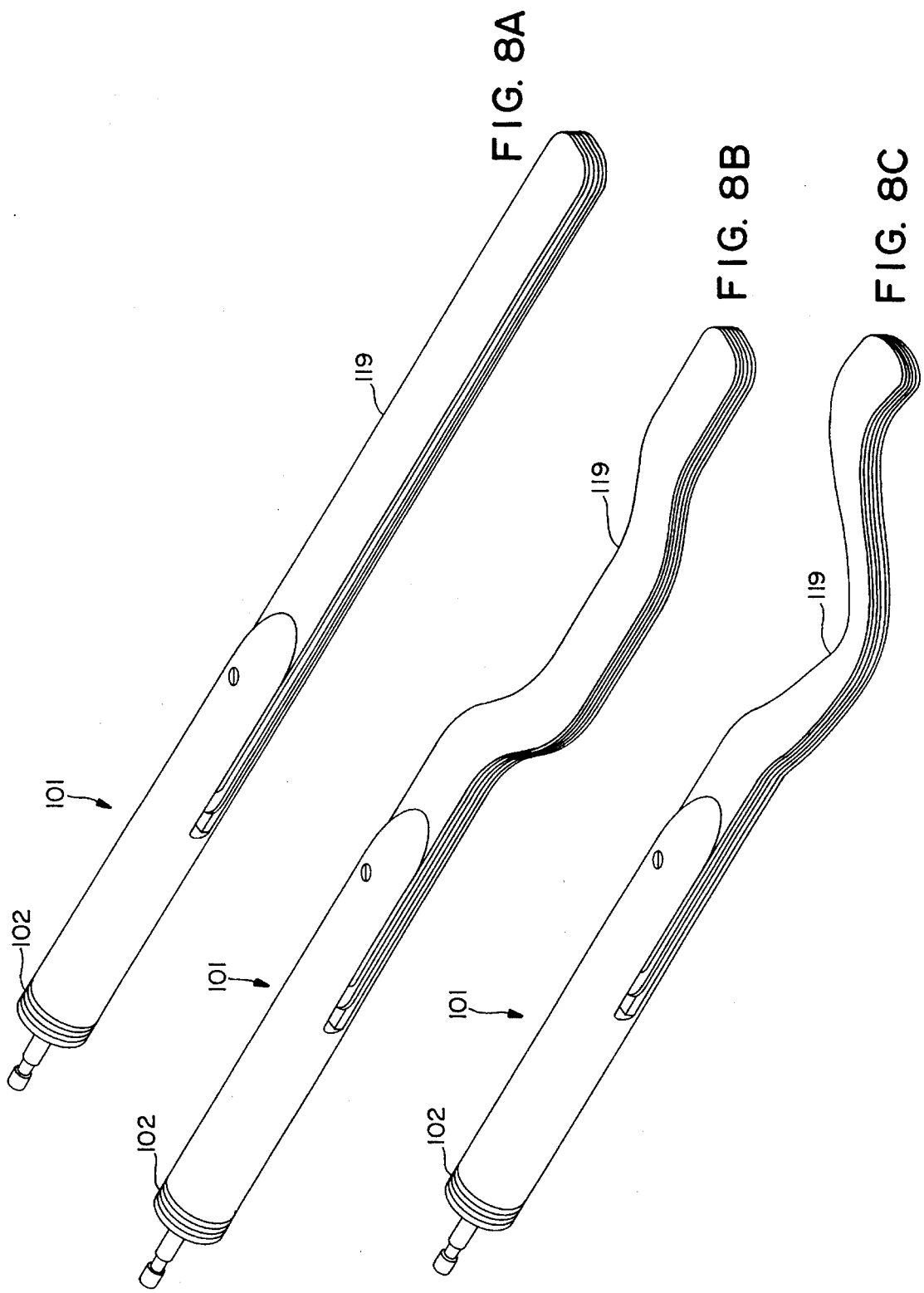

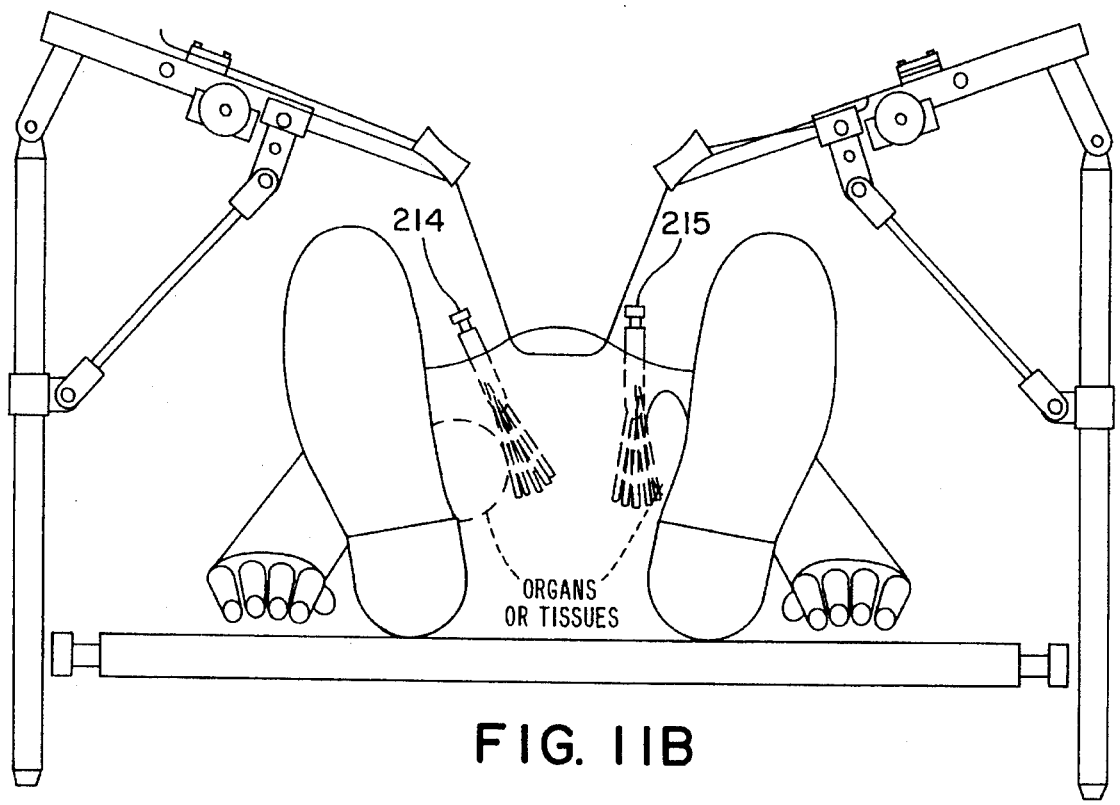
FIG. IIB

SUSPENSION AND RETRACTION SYSTEM FOR ENDOSCOPIC SURGERY AND METHOD FOR USING SAME

CROSS-REFERENCE TO RELATED APPLICATIONS

This application is a continuation-in-part of copending application Ser. No. 07/761,375, filed Sep. 18, 1991.

BACKGROUND OF THE INVENTION

1. Field of the Invention

This invention relates to surgical devices and a method for using the same in endoscopic surgery (also known as closed surgery) wherein the surgeon gains access to the surgical site via one or more portals. More particularly, the invention relates to devices and a method for retracting internal organs and distending the walls of a body cavity so that structures can be seen in an adequate panoramic endoscopic view.

2 Description of the Prior Art

U.S. Pat. No. 2,202,748, (Solo) discloses a septum splint for molding the nasal septumi straight following the operation of sub-mucous resection or in traumatic conditions wherein it is desirable to bring into contact or approximation the layers of the nasal septum. The splint comprises a pair of body members, oppositely arranged screws engaging holes in the two body members for adjusting them towards and away from each other, a stationary blade extending from the outer side of each member, blades pivoted to each member, a cam carried by each member and engaging parts of the pivoted blades for moving them outwardly into a fan shape, and a screw engaging a threaded hole in each member for moving the cam against the parts of the blades.

U.S. Pat. No. 4,608,965, (Anspach, Jr., et al.) discloses an endoscope retainer and tissue retracting device comprising a soft plastic cylindrical tube slidably mountable on the probe portion of the endoscope, the end of the soft plastic cylindrical tube having a slightly reduced diameter to have a friction holding fit over the end of the endoscope, a plurality of slits located around the soft plastic cylindrical tube adjacent the end of reduced diameter, said slits forming a plurality of flexible strips which bend to extend radially outwardly when their ends are brought together by sliding the other end of the soft plastic cylindrical tube along on the probe portion of the endoscope toward the end having the friction holding fit over the end of the endoscope, and means for fixing the other end of the soft plastic cylindrical tube to the endoscope with the strips extending radially outward.

U.S. Pat. No. 4,654,028, (Suma) discloses an incision opening expansion holder for inosculation comprising a cylindrical hollow elongated outer tube having a longitudinal axis; a cylindrical elongated inner tube having a longitudinal axis and a first end and a second end and being of a diameter smaller than the diameter of said outer tube and slidably inserted into said outer tube; a grip device fixed to the first end of said inner tube; and a plurality of resilient wires, each having one end thereof attached to the second end of the inner tube and another end thereof having a round ball structure attached thereto, the plurality of wires being shaped to extend radially outward from the axis in a smooth curve. The inner tube is of sufficient length to extend said second end to an end of the outer tube in an opened position and to retract the attached wires to be completely within the outer tube in a closed position. The wires are of sufficient resilience and axial length so as to be compressed into and fit completely within the outer tube in the closed position, and to extend completely outside of said outer tube in the opened position with the round ball structures located at the ends of the wires being spread out radially and with the wires being resiliently expanded to a circular shape.

U.S. Pat. No. 3,823,709, (McGuire) discloses a table supported surgical retractor and pelvic support which comprises an operating table supported surgical retractor assembly for individual retracting blades which hold the various parts of the body away from the surgical area.

U.S. Pat. No. 3,858,578, (Milo) discloses a surgical retaining device comprising a retaining arm, the rigidity of which is controlled by a fluid actuated operating apparatus. A surgical instrument is attached to the retaining arm. By activating the operating apparatus, the arm can be made flexible as the instrument is being positioned and rigid once the instrument is in place.

U.S. Pat. No. 4,099,521, (Nestor, et al.) discloses a surgical retractor adjustable mounting apparatus comprising an arcuate frame sized to fit concentrically at a spaced distance about the head. Retractors, retaining the mouth and lips in open position for vertical and lateral exposure during mouth and jaw surgery, are adjustably suspended from the frame by an adjustable universal connector. The frame is mounted on an upstanding support from the operating table by connecting means providing adjustability thereof for universal spatial orientation.

U.S. Pat. No. 4,457,300, (Budde) discloses a surgical retractor provided for retaining tissue, membrane and organs in a retraced position from an incision during a surgical procedure which includes a tiltable ring having an outwardly extending channel to receive arm support means having a projection captured within and movable along the channel. Retractor arms are mounted to the arm support means such that they pass below the ring and extend inwardly toward the incision so as to not obstruct the surgeon's line of sight or movement of the hands along the ring.

U.S. Pat. No. 4,573,452, (Greenberg) discloses a surgical holder for a laparoscope or the like wherein a selectively tensionable cable-type component is released for moving the laparoscope almost into its desired position and then tensioned into a rigid structure; and then a ball and socket joint is rendered operational to complete the moving of the laparoscope, if need be, to precisely position the instruments in its required anatomy-viewing position.

U.S. Pat. No. 4,593,681, (Soni) discloses a stabilizing device for use in arthroscopic and endoscopic surgery comprising a relatively thin, flat, flexible plate of plastic material and adapted to be placed against a patient's body at the area where penetration is made by the scope sheath. The plate is formed with a predetermined sized central hole and the sheath is slidably insertable through the hole and has an interference fit with the surrounding plate material. The plate provides a stable base for the scope to be slidable moved with respect to the plate to adjust the depth of penetration.

U.S. Pat. No. 4,621,625, discloses a leg traction device for supporting the leg and applying axial force to the leg wherein a rigid vector bar is positioned above the knee and lower leg and a pulley system including a cable and weight connected at one end to a leg supporting structure and at the other end to the vector bar.

U.S. Pat. No. 4,632,458, (Brown, et al.) discloses a chair back height adjustment mechanism for a chair having a chair back supporting standard and a chair back bracket with a chair back or backrest mounted thereon. The mechanism includes a rack gear on the chair back standard, a pinion gear supported in a bearing on the chair back bracket, a worm gear coaxial with the pinion gear, and worm threads on a dial shaft supported on the bracket. Rotation of the dial causes the worm member to rotate the worm gear and the pinion gear whereby the bracket supporting the pinion gear is translated in relation to the chair back standard.

U.S. Pat. No. 4,690,647, (Dalglish) discloses an intravenous tube assembly to supply intravenous fluid to a patient. The assembly comprises an intravenous fluid container, held by a stand, and connected to one end of an intravenous fluid tubing, the other end of the tubing connected to a patient, and a mast assembly which has an elongate resilient mast and a movable tip and a base. The base is fixed to a structure proximate the patient, e.g., a bed frame; and the tip carries a tube holder which releasably holds a segment of the intravenous tubing leading to the patient. The mast permits patient movement by deflecting to follow the patient and rebounding upon return of the patient to prevent an excess of residual intravenous tube in the vicinity of the patient.

U.S. Pat. No. 4,809,687, (Allen) discloses a medical stirrup for supporting a patient's limb in a desired attitude is disclosed. The limb is cradled in a shell lined with soft material. The limb is retained in the shell by adjustable bands. The shell is suspended from a support by adjustable straps; and the attitude of the limb is controlled by the adjustment of the straps and the positioning of the support.

U.S. Pat. No. 4,850,563, (Grout) discloses an adjustable desk frame comprising a base consisting of a pair of vertically extending transversely spaced members; a sub-frame vertically movably adjustably supported by the base, and including a pair of vertically extending members telescopically received within the vertical members of the base; and a drive assembly to move the sub-frame vertically relative to the base, the drive assembly including a rack gear attached to each vertical member of the sub-frame, a pinion gear meshingly engaged with each rack, with the pinion gears being rotatably supported by the base, a shaft extending between the two pinions to transmit rotary power therebetween, a worm gear meshingly engaged with one of the pinions, and rotatably supported by the base, and a drive shaft fixed to the worm gear and extending therefrom to a position manually operably by a user of the desk, the drive shaft adapted to be supported by the sub-frame.

U.S. Pat. No. 4,867,404, (Harrington, et al.) discloses a flexible holder for a cytoscope or the like which is equipped with a clamping assembly which permits the holding of various sized instrument shafts. The clamping assembly comprises a vertically adjustable spring-biased C-shaped open-sided region, which is telescopically movable in a tubular housing and releasably urged to an open position. The instrument shaft is received sideways into the C-shaped jaw and retained between the jaw and a pair of circumferentially opposing notches of the tubular housing.

U.S. Pat. No. 4,926,849, (Downey) discloses an apparatus for separating vertebrae, i.e. adjacent first and second vertebrae, during surgery comprising: a support; first and second grips associated with the support and being sized and structured to grip the first and second vertebrae, respectively; a first movement assembly, associated with the first grip, capable of moving the first grip to a desired location relative to the second grip; and a second movement assembly, associated with the second grip, capable of moving the second grip to a desired location relative to the first grip.

U.S. Pat. No. 4,932,395, (Mehdizadeh) discloses a hemilaminectomy retractor attachment device, adapted for use with prior art retractors, including two hook-shaped members that are joined together by a length of strong flexible cord. The hook-shaped members are narrow enough to fit between spinal bones to brace against the spinal ligaments, and the cord is engagable with the retractor arm.

U.S. Pat. No. 4,945,896, (Gade) discloses a surgical retractor having a generally flat malleable blade with a miniature metabolic parameter sensor embedded or removably inset into the blade to monitor tissue viability of the tissue underlying the retractor.

U.S. Pat. No. 5,003,967, discloses a traction support member for holding an individual's arm and hand in elevated position. The traction support member includes an upright member which is disposed between first and second transverse members. The upright member is movable about a vertical axis universal positioner; and the first transverse member is movable about a horizontal axis through an attachment coupling at which the first transverse member is attached to the upright member.

U.S. Pat. No. 5,065,739, (Forrest, et al.) discloses a retractor support assembly comprising a rocking arm, means for flexibly connecting the retractor to the rocking arm and weight means, connected to the rocking arm, for pulling the retractor in a generally upward direction.

As may be readily ascertained, few of the aforementioned devices refer to endoscopic surgery. By endoscopic surgery is understood surgery during which the surgeon gains access to the surgical site via one or more portals. Through these portals, endoscopes, instruments and the like are inserted. The endoscopic surgical procedures include, but are not limited to, arthroscopy, laryngobronchoscopy, laparoscopy (pelviscopy), gastroenteroscopy, and laparoscopic surgery of the female reproductive organs.

Endoscopic surgery would be preferred over open surgery for most procedures because it greatly reduces trauma and risk of general anesthesia-related complications to the patient and saves the costs associated with performing the surgical procedures. However, the below outlined disadvantages had not allowed full expansion in the areas in which this type of surgery could be competently performed.

To date, it is necessary to infuse the body cavity with $CO_2$ or $N_2O$ in order to achieve sufficient expansion of the cavity in order to obtain proper panoramic viewing. A major drawback of the present technique, as explained in the example of laparoscopy, is the necessity to maintain an air-tight boundary between the inside and outside of the body cavity, i.e., the abdomen, in order to obtain proper visualization of structures. Another important handicap is the fact that in spite of the floating effect created by the gas, it is still not possible to reach deep-seated areas. Other disadvantages include image distortion and patient discomfort.

SUMMARY OF THE INVENTION

Accordingly, a primary objective of the present invention is to provide a system particularly useful in distending the anterior wall of a body cavity and in retracting all superficial organs in order to obtain a good panoramic view of the body cavity when performing closed surgery, preferably arthroscopic, thoracoscopic or laparoscopic surgery, more preferably deep laparoscopic surgery or selective large bowel, pancreatic, splenic gastric, hepatic laparoscopic surgery or laparoscopic surgery of the female reproductive organs.

Using the system of this invention, substantial improvement can be obtained in the efficacy of treatment since the operating surgeon can easily pull the anterior wall of the body cavity far enough away so as to be able to obtain an adequate panoramic endoscopic view while not worrying about maintaining adequate intro-cavital pressure. This greatly enhances the potential for developing more advanced surgical techniques. The system allows the retraction of internal organs, especially those located in the abdominal cavity such as bowels, to the sides of the body cavity to allow access to such structures like, for instance, the retroperitoneum or selected intro-abdominal structures. This second step must be performed endoscopically.

It is a further object to provide a lateral suspension device consisting of means for attaching the device to the side of the table, means for holding one end of one or more wires and a sliding assembly for adjusting the suspending force of the wires. Optionally, the lateral suspension device may comprise a malleable arm, a shaft for holding the malleable arm, and a portion comprising means for fixing the position of the retractor.

Still another object to this invention is to provide a novel retractor comprising a plurality of blades for retracting internal organs, said blades being slidably moved to adjust the span of the blades. A retractor according to the invention, can therefore be used generally, in endoscopic surgical procedures, so that it can be located in the body cavity and pulling means can easily pull the desired internal organ to the side, selectively exposing thereby the body structure to be viewed. The retractor can be used as a stand alone device, or in conjunction with one or more lateral suspension device.

A suspension and retraction system comprising at least one lateral suspension deice operably connected with an overhead device and a retractor is also encompassed by the present invention.

The present invention is further generally characterized in a method of exposing any desired portion of body cavity during endoscopic surgical procedures comprising the steps of (a) locating at least one lateral suspension device on each side of the patient; (b) passing a wire through a muscular layer into a body cavity, along a predetermined distance under the anterior wall of the body cavity, and out of the body cavity through a muscular layer; (c) connecting each end of said wire to a lateral suspension device on opposite sides of the patient; (d) repeating steps (a)–(c), as needed, to form a mesh sufficient to support said anterior wall of the body cavity; and (e) tensioning said wire to support said anterior wall of the body cavity.

These and other advantages and objects of the invention will be apparent from the following description of the preferred embodiments taken in conjunction with the accompanying drawings and the appended claims.

BRIEF DESCRIPTION OF THE DRAWING FIGURES

FIG. 1A shows a side view of an embodiment of a complete suspension and retractin system in its operable mode.

FIG. 1B is a plan view of FIG. 1A.

FIGS. 8A, 8B and 8C illustrate different blade configurations usable with the retractor of FIG. 6.

FIGS. 11A and 11B illustrate the utilization of the lateral suspension device of the present invention in conjunction with the preferred retractor of the present invention.

DETAILED DESCRIPTION OF THE INVENTION

The invention will now be explained by way of examples of the devices, system and method designed fo ruse in deep laparoscopic surgery.

Figure 2:
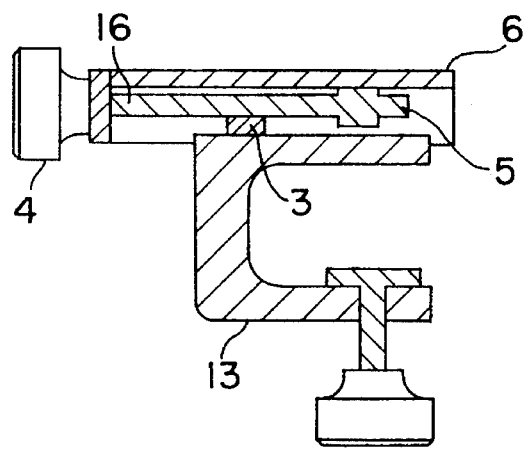
FIG. 2 shows a sliding assembly utilizable with the suspension system of FIGS. 1A and 1B.

As illustrated in FIGS. 1A, 1B and 2, the lateral suspension device 17 comprises a clamp 1 which attaches to the side, preferably a rail, of the surgical table 2, bed or any other kind of furniture in close proximity to the patient. The clamp 1 is in fact the distal section of a sliding assembly 6 which supports a vertical rod 15 which is preferably about 85 centimeters long. The sliding assembly has an excursion of about 10 centimeters to and from the side of the table, and this excursion is obtained by turning, preferably manually, a nut 4, which is preferably knurled, which rotates a screw 5. The screw 5 meshes with rack 3 attached to rod clamp 13, the rod clamp being slidably retained in the sliding assembly 6. The above described sliding assembly is an example of means for adjusting the suspending force of the wires. These means may vary without affecting the concept of the invention. As an alternative, the vertical rod 15 may have teeth (not shown) along its internal side and its movements up or down are controlled with a ratchet (not shown) located on the sliding assembly 6. The axial advancement of the vertical rod would then determine the amount of suspending force. The vertical rod 15 may have an angle 14, preferably of about 80 degrees, located preferably about 35 centimeters from its distal end 16. This distal end 16 has a portion 18 for securing one or more wires directly or for holding at least one means for attachment to one end of the one or more wires. An example of such means for holding wires is a clamp. The means of wire-attachment may vary without affecting the concept of the invention. Optionally, the lateral suspension device may comprise a malleable arm, a shaft for holding the malleable arm, and a portion comprising means for fixing the position of the retractor. The complete unit (with exception of the wires) is made of rigid material which is conventionally used for manufacturing surgical devices. Preferably, stainless steel is used.

The wires can be made from any materials which are conventionally used for manufacture of needles and wires suitable for use in surgical procedures. Stainless steel is illustrative of such suitable materials that may be used in manufacturing the wires for use in the lateral suspension device 17 of this invention. The configuration, diameter or cross-section along the length of the wires can be varied depending upon the endoscopic procedure. For instance, wires can be tapered throughout their length to a sharp tip. The configuration of the wires can be of any conventional shape and can range from, but is not limited to, solid, hollow, circular, semi-circular, oval, rectangular, hexagonal or polygonal configuration. The wires are not designed to remain in the tissue after the surgical procedure is completed. The wires can be conventionally sterilized for reuse, if necessary, although it is preferable to discard them since the unit cost is low and disposal avoids any subsequent sterilization and storage problems.

The lateral suspension device 17 of the present invention can be any size from micro to macro depending on the type of the endoscopic procedure for which it is designed for use without effecting the concept of the invention. All components of the lateral device (with exception of the wires) are intended for indefinite reuse.

Figure 3:
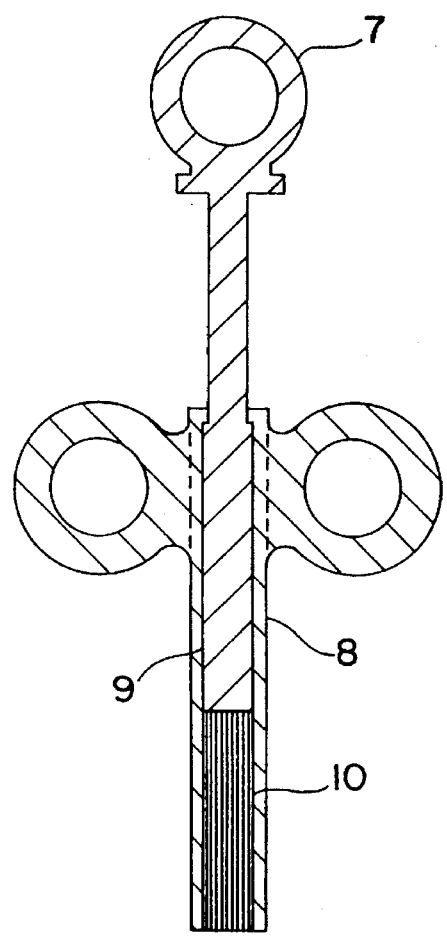
FIG. 3 is a sectional view of a retractor according to the present invention in a "closed" position.
Figure 4:
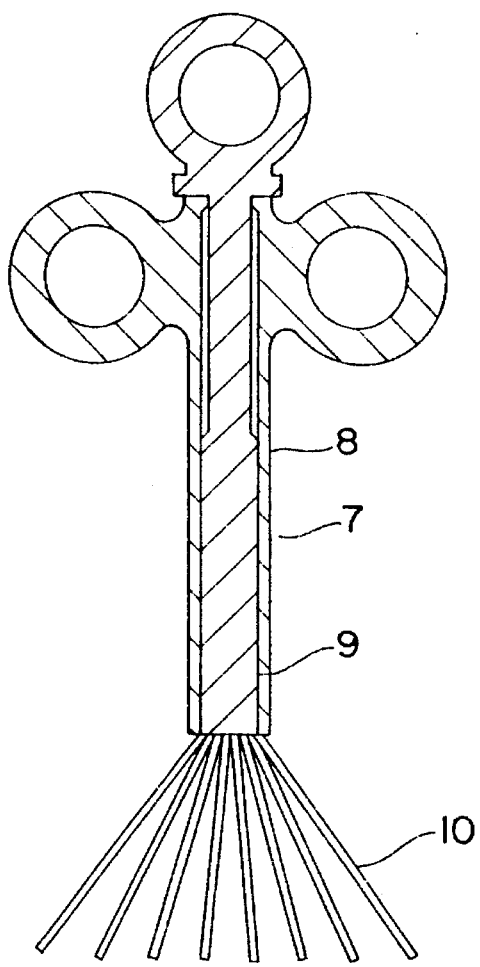
FIG. 4 is a sectional view of the retractor of FIG. 3 in an "open" position.
Figure 5:
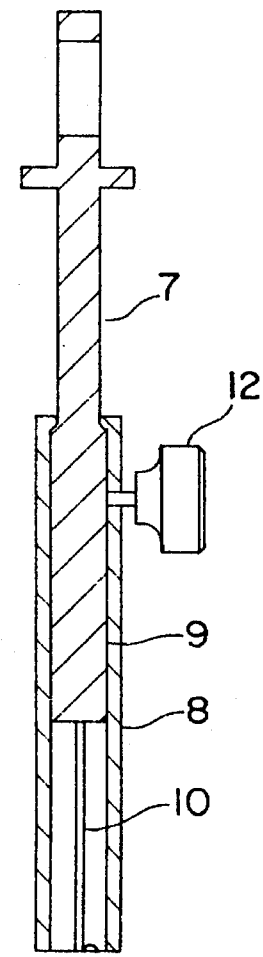
FIG. 5 is a side sectional view of the retractor of FIG. 3.

In one embodiment of the invention, as shown in FIGS. 3–5, a retractor 7 comprises a cylindrical tube 8, a plunger 9, slidably received within the tube 8, and blades 10. Various mechanisms can be accommodated on the tube 8 to hold one or more, preferably four to eight, blades 10. The blades can be made from any suitable rigid material, preferably stainless steel. Optionally, they may be covered with a teflon coating and the like. The tube 8 provides a stable cover for the plunger 9 holding the blades 10 to be slidably moved with respect to the sheath to adjust the span of the blades and the depth of penetration. The blades can vary in length and thickness.

After the retractor 7 has been inserted, the blades can be pushed out and locked din place by lock screw 12.

After the retractor 7 has been inserted and its blades 10 have been put in traction, retracting organs, the top of the retractor is attached to the distal end 16 of the suspension device. In this fashion, the retractor becomes autostatic and can still be adjusted from time to time by the surgeon. As mentioned already, the retractor can be used as stand alone device, or in conjunction with one or more lateral suspension devices, or combination of both.

In the construction of a working model of the retractor 7, the blades 10 were in length from 12 to 20 centimeters and in thickness up to about 1 mm, and had a span of 7 to 9 cm.

A system for retracting any internal organs and distending the walls of the body cavity comprises operably connected at least one lateral suspension device 17 operably connected with the retractor 7 as shown in FIG. 1A and FIG. 1B.

Now, a method of retracting internal organs and distending the walls of the body cavity will be explained by way of example of retracting bowel to the right side, the transverse colon cephalad and the descending colon, and distending the walls of abdominal cavity, and exposing thereby the infra-pancreatic retroperitoneum.

In operation, at least one lateral suspension device is used on each side of the patient. Preferably, two lateral suspension devices are used on each side of the patient. A needle, preferably of a stainless steel monofilament size 4, is introduced into the muscular layer of the abdominal cavity of the patient at the level of the right upper quadrant parallel to the costa margin, and threaded twice, leaving the wire embedded within the abdominal wall. The needle is then cut out from the wire. The two strands of wire are attached to a suspension device and then adjusted to the desired tension. A similar procedure is done in a horizontal plane lateral to the rectus muscle starting at the level of the right upper quadrant towards the right lower quadrant. About 5 centimeters of the same wire is passed subcutaneously through the muscle layer before being pulled above the surface of the skin and reintroduced through the same skin puncture and passed along the muscle layer of the skin and reintroduced through the same skin puncture and passed along the muscle layer to make a 12 to 14 centimeter suspension area. The needle is cut from the wire, and the two ends of wire are attached to the suspension device and tightened as required. The procedure described for the right upper quadrant is repeated at the level of the right lower quadrant. The same procedure is done on the opposite side. It is not essential to obtain "perfect symmetry". If it is feared that the bare wires could damage the abdominal wall, a coating of teflon or even silicon could be added to the wire.

The lateral suspension device is fixed to the table so it does not become a nuisance for the surgeon or his or her assistants. It typically will be used to the left of the center of the abdomen at the umbilical level using a stainless steel monofilament. Maximal traction is not obtained until the endoscope has been introduced into the cavity through the cannula of a trocar.

Under vision, it is possible to adjust the tension of the wires to the ideal viewing point.

Using one or more retractors, it is then easy to pull the small bowel to the right side, the transverse colon cephalad and the descending colon to the left, exposing the infra-pancreatic retroperitoneum. Similarly, one can easily expose selectively any portion of, for instance, the large bowel, pancreas, spleen, stomach, thorax, liver, lungs and heart, not to mention uterus, ovaries, bladder, lymph nodes or any pathologies located in the thoracic, intra-abdominal or other cavities.

Figure 6:
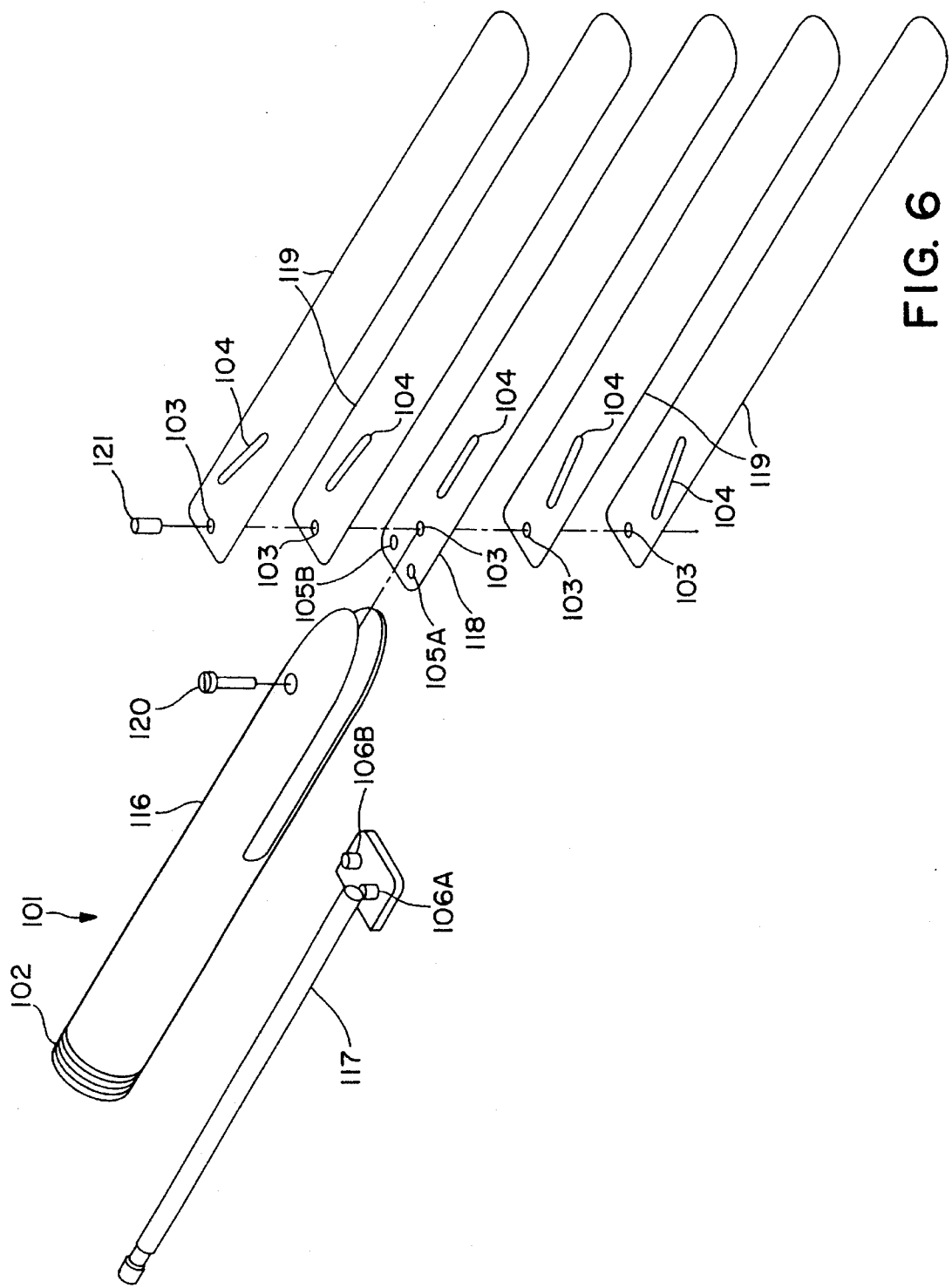
FIG. 6 is an exploded view of a preferred embodiment of the retractor of the present invention.

FIGS. 6–8 illustrate preferred embodiments of a retractor for use in the present invention. The retractor is designed so as to be insertable into the body cavity through a portal of limited diameter and then be expanded to provide a "fan" within the patient.

The retractor 101 is composed of a body 116, a pull/push rod 117, a fan assembly 118, 119 and a manual adjustment device 122 or 123. The body 116 holds all the pieces of the retractor. At one end, the body holds the blades (118, 119) via a guide pin 120. At the opposite end, the manual adjustment devices (122, 123) are attached as by screw threads 102. Sliding in the center of the body 116 is the push/pull rod 117 which connects the blades (118, 119) to the manual adjustment device (122 or 123).

The pull/push rod 117 transfers the mechanical action of the manual adjustment devices (122 or 123) to the center blade 118 of the fan assembly. Depending on the set of blades used, pushing the rod will cause the blades to open or close into a "fan" shape. Similarly, pulling the rod will cause the blades to close or open.

The fan assembly (118, 119) is composed of a plurality of flat blades. The number of blades can vary, i.e., there can be an odd or even number of blades and there can be a few or many blades. Preferably, there are an odd number of blades, so as to easily obtain a symmetrical "fan". Typically, 5, 7 or 9 blades are used, although few or greater can also be used. Usually, the number of blades will be determined by the needs of the particular operation to be performed, e.g., by the size of the organ to be retracted.

The blades are not restricted to any one flat shape. They can have an infinite array of forms so long as the shape does not interfere with the opening and closing of the fan, nor does it interfere with insertion of the retractor through the chosen portal. Various blade shapes are illustrated in FIGS. 8A, 8B and 8C. (For ease of description, the blades will be illustrated by flat, straight blades, as shown in FIG. 8A hereinafter. However, it should be borne in mind that any shape can be utilized, as needed.)

As shown in FIG. 6, each blade has a hole 103 therethrough which is located substantially on the longitudinal axis of the blade. All the blades are held together by a pin 121 which is received in the holes 103 so as to provide a common axis of rotation for said blades about said pin 121.

Each blade has an elongate channel 104 therethrough. One blade 118 has the channel 104 located on and aligned with the longitudinal axis of the blade. Respective pairs of the remaining blades have the channel aligned at substantially equal but diverging angles relative to the longitudinal axis of the blade. When assembled, guide pin 120 passes through each of the channels 104 and is fixed in place in the body 116. Thus, when the blades are moved forward or backward within the body 116 by push/pull rod 117, the blades rotate about pin 121 and the degree of rotation of the blade will be determined by the angle of the channel 104 with the longitudinal axis of the blade 119.

The center blade 118 is provided with two holes 105A, 105B therethrough which receive pegs 106A, 106B, respectively, formed on push/pull rod 117. Thus, the longitudinal motion of the push/pull rod can be transmitted to the blades. (In FIG. 6, the blades 119 have been arranged symmetrically about blade 118, i.e. equal numbers of blades 119 above and below blade 118 and the further above or below blade 118, the greater the degree of rotation away from blade 118, albeit in opposite directions. However, any stacking arrangement of the blades can be utilized, as long as it does not interfere with the operation of the retractor.)

Figure 7A:
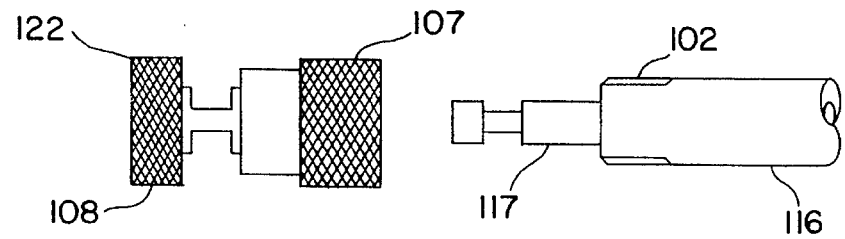
FIGS. 7A and 7B illustrate different activation mechanisms for the retractor of FIG. 6.
Figure 7B:
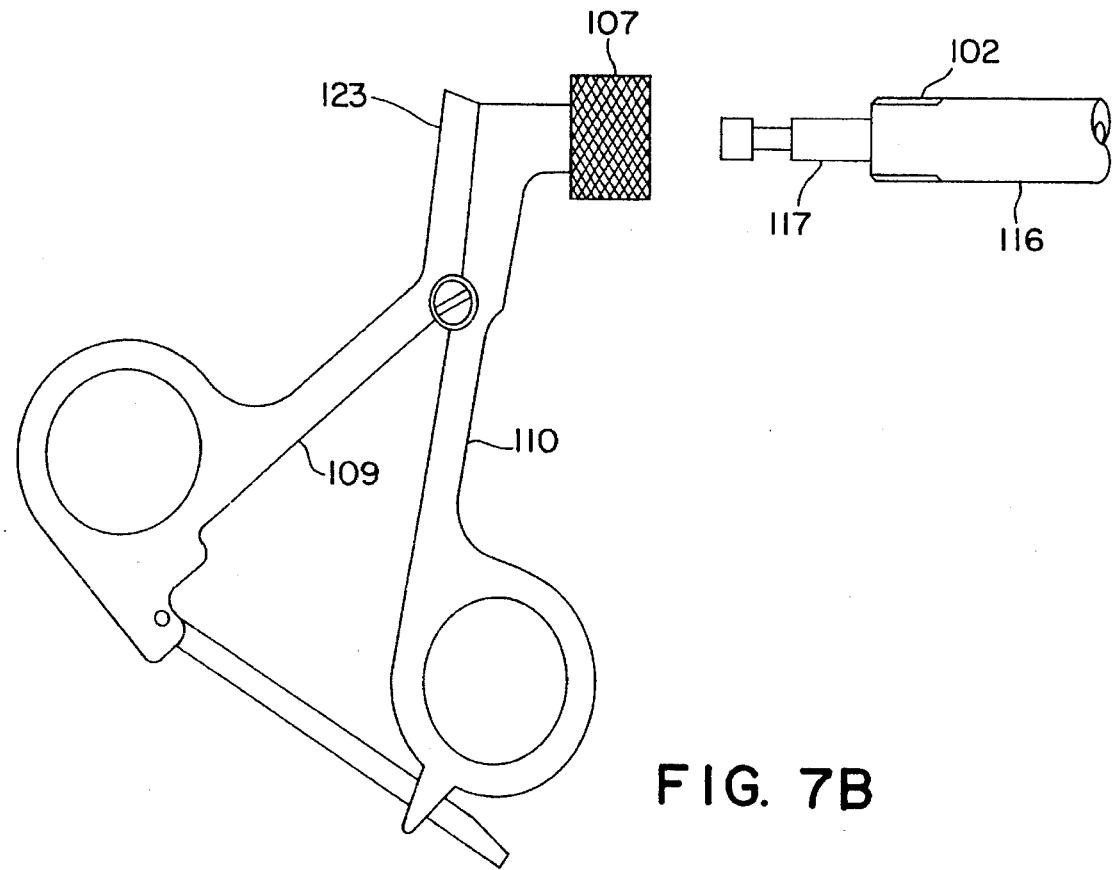

As shown in FIGS. 7A and 7B, the retractor body may be fitted with various mechanical adjustment devices for operation of the push/pull rod 117. FIG. 7A illustrates a screw knob 122 which is connected to the retractor body 116 by a threaded connector 107 which engages screw threads 102. Turning the knurled knob 108 one way or the other will either push or pull the push/pull rod 117, dependent on the direction of rotation. FIG. 7B illustrates a scissor grip 123 which is connected to the retractor body 116 by a threaded connector 107 which engages screw threads 102. Compressing or expanding the scissor arms 109, 110 toward or away from each other will pull or push the push/pull rod 117. Any other conventional adjustment devices can be utilized, the choice between them being the surgeon's preference.

Figure 9:
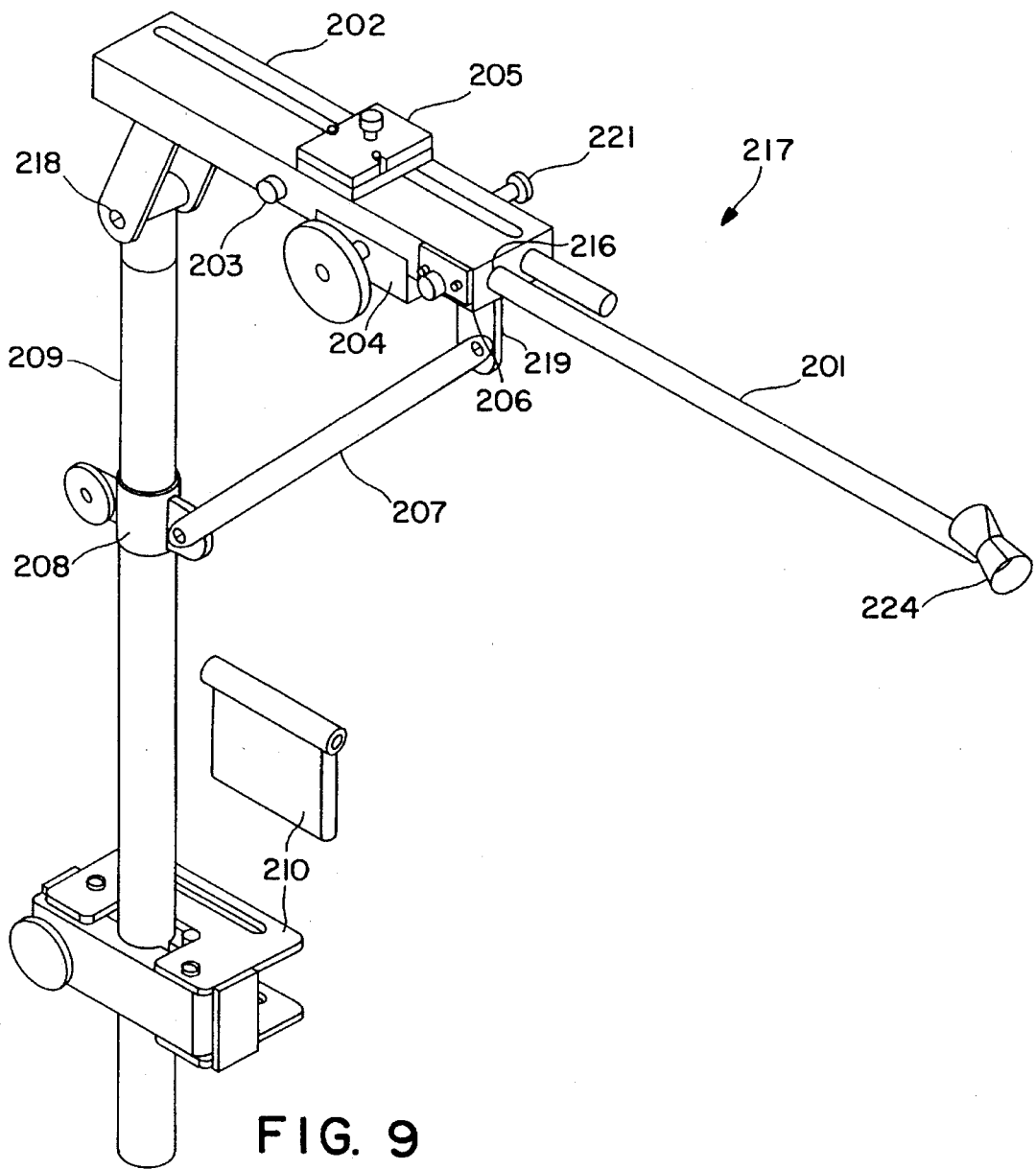
FIG. 9 is a perspective view of the lateral suspension device according to the present invention.

FIG. 9 illustrates a particularly preferred embodiment of the lateral suspension device of the present invention. In particular, the lateral suspension device 217 comprises a horizontal arm 201, a pivoting body 202, a vertical support pole 209 and a table clamp 210.

The horizontal arm 201 is used to adjust the wire position relative to the patient's body. The arm 201 is slidingly received within a bore 216 formed in pivoting body 202 so that the distance between the trumpet guide 224 and the pivoting body 202 may be increased or decreased. The arm 201 may be fixed into place by a locking mechanism such as thumb screw 203. At the end of the arm nearest the patient, a trumpet guide 224 is provided. This guide allows the wire to bend smoothly from the lateral suspension device to the patient without risk of bending damage to the wire.

The pivoting body 202 carries a gear system 204 for positioning a movable clamp 205 at any position from one end of the pivoting body 202 to the other. Once the proper position is located, the gear system is then locked in place by either a ratchet mechanism or a set screw 221 (as best seen in FIG. 9) located within the gear system. The gear system itself can be anything from a worm gear to a spur gear, as long as its method of operation does not interfere with the function of the arm 201.

The pivoting body is provided with two clamps 205 and 206 for holding wires. As previously noted, clamp 205 is adjustable via the gear system 204 so that it may increase or decrease the tension in the wire as it travels from one end of the pivoting body 202 to the other. The fixed clamp 206 is mounted on the side of the pivoting body 202 to prevent it from moving. Both clamps may work with a system that compacts the wire between two toothed plate. Alternatively, any other conventional means for gripping a wire may be utilized.

The pivoting body 202 may pivot about a horizontal axis, as defined by pin 218, 180° from straight down to straight up, and may be locked in place at these extremes as well as anywhere in between. This "locking" is achieved by support rod 207 which is pivotally connected to a lug 219 formed on pivoting body 202 and which is also pivotally connected to a pole clamp 208 which is slidable on the vertical pole 209, but which may be clamped thereto at any vertical location. Once the approximate angular orientation of the pivoting body 202 is located, the pole clamp is locked in place to prevent further movement.

The table clamp 210 attaches the vertical pole 209 to the operating table. This clamp allows attachment anywhere along he edge of the operating table. This clamp allows vertical movement of the support pole 209, when unclamped, and prevents vertical movement of the support pole, when clamped. This clamp allows rotation of the vertical pole 209 about its vertical axis, when unclamped, but prevents rotation thereof when clamped.

Figure 10A:
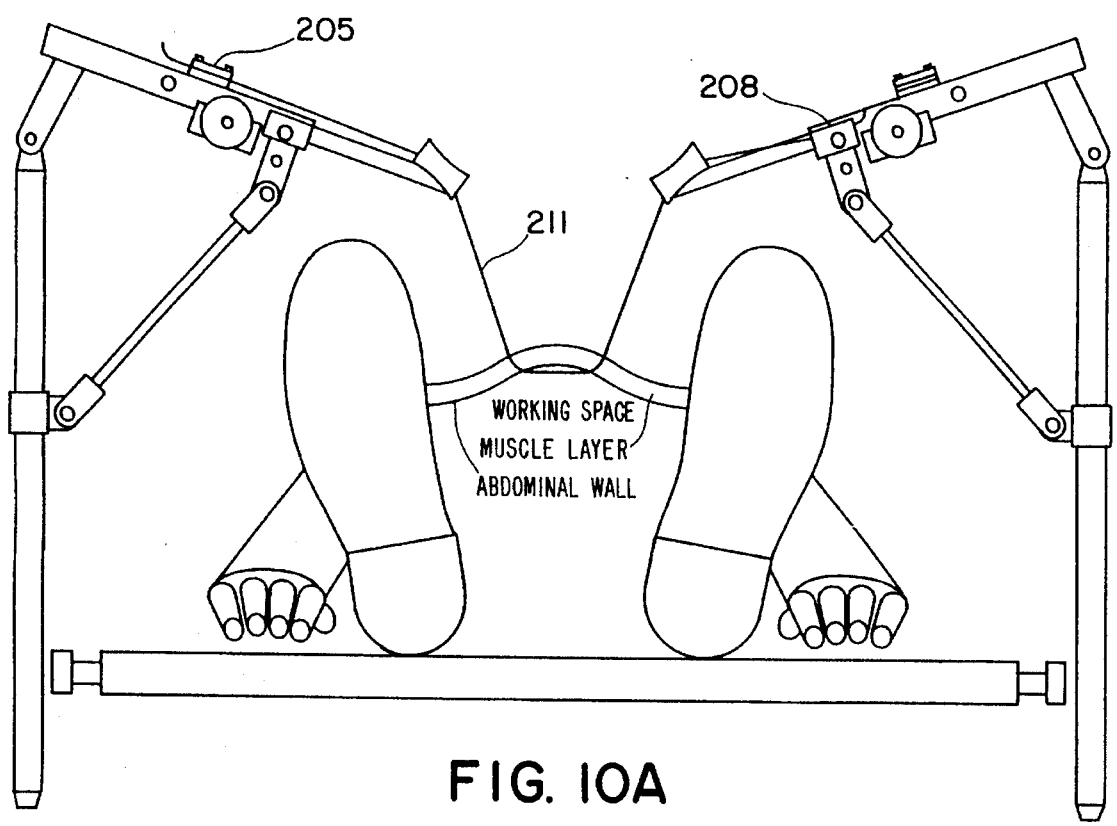
FIGS. 10A and 10B illustrate the utilization of the lateral suspension device of the present invention.
Figure 10B:
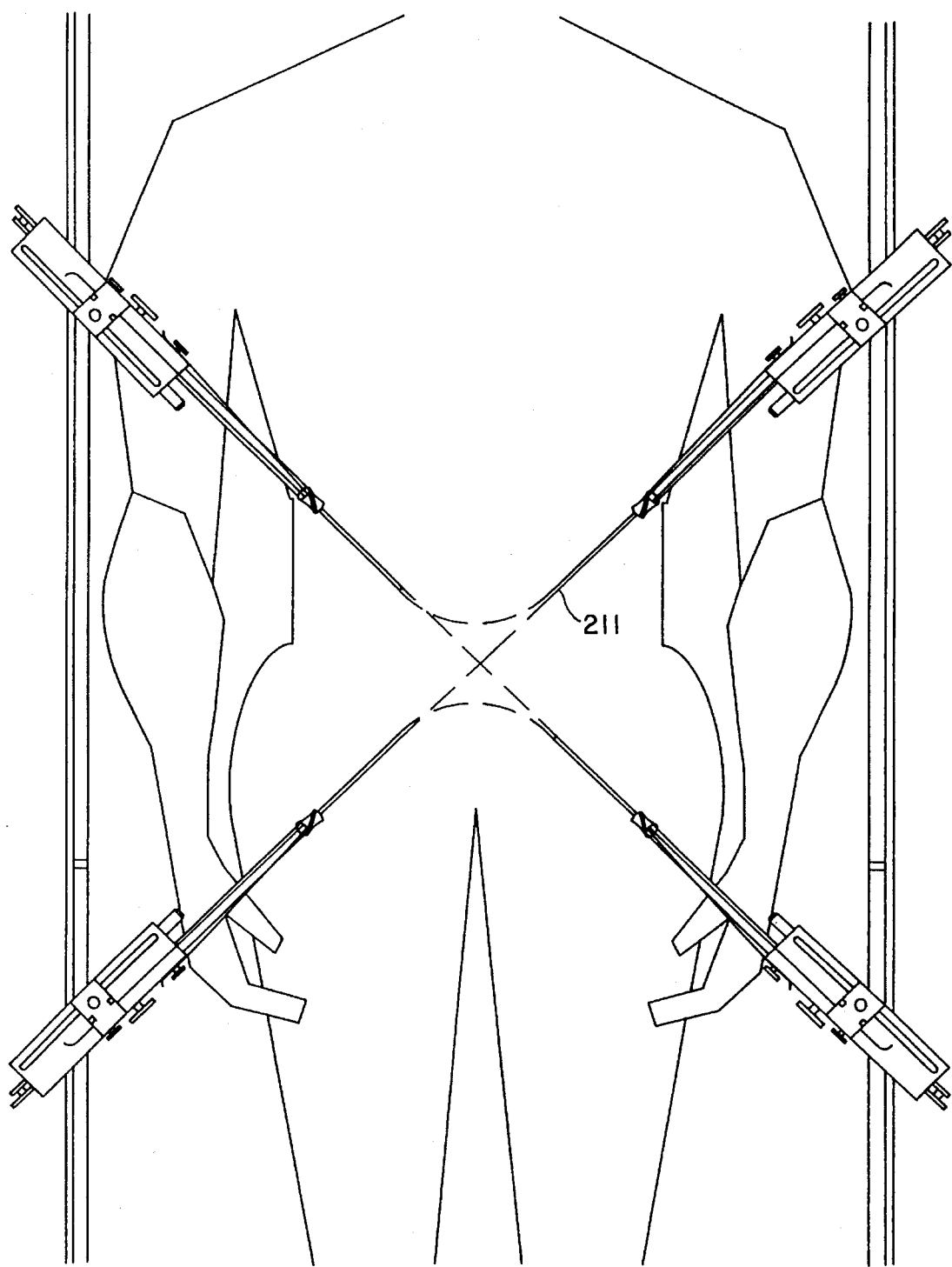

To use the lateral suspension device of the present invention, the surgeon prepares the patient temporarily with $CO_2$ or $N_2O$ gas pressurization. Once the abdominal cavity is pressurized, a stainless steel wire is passed through, using a long needle. The wire travels through the muscular layer into the abdominal cavity. The wire travels a desired distance under the anterior wall to create a suspension area, and then passes out through the muscular layer. The needle is then removed and each end of the wire is attached to a different arm. One end of the wire 211 connects to the fixed clamp 206 on one arm and the other end of the wire connects to the movable clamp 205 on another arm, as shown in FIG. 10A. By pull the adjustable clamp 205 away from the patient (via the gear system 204) the tension in the wire is increased and thus supports the anterior wall. The number, location and tension of the wires used will determine the working space within the abdomen. FIG. 10B shows a possible set-up using four wires and four arms. Once the wires are in place, gas pressurization can be neglected.

Figure 11A:
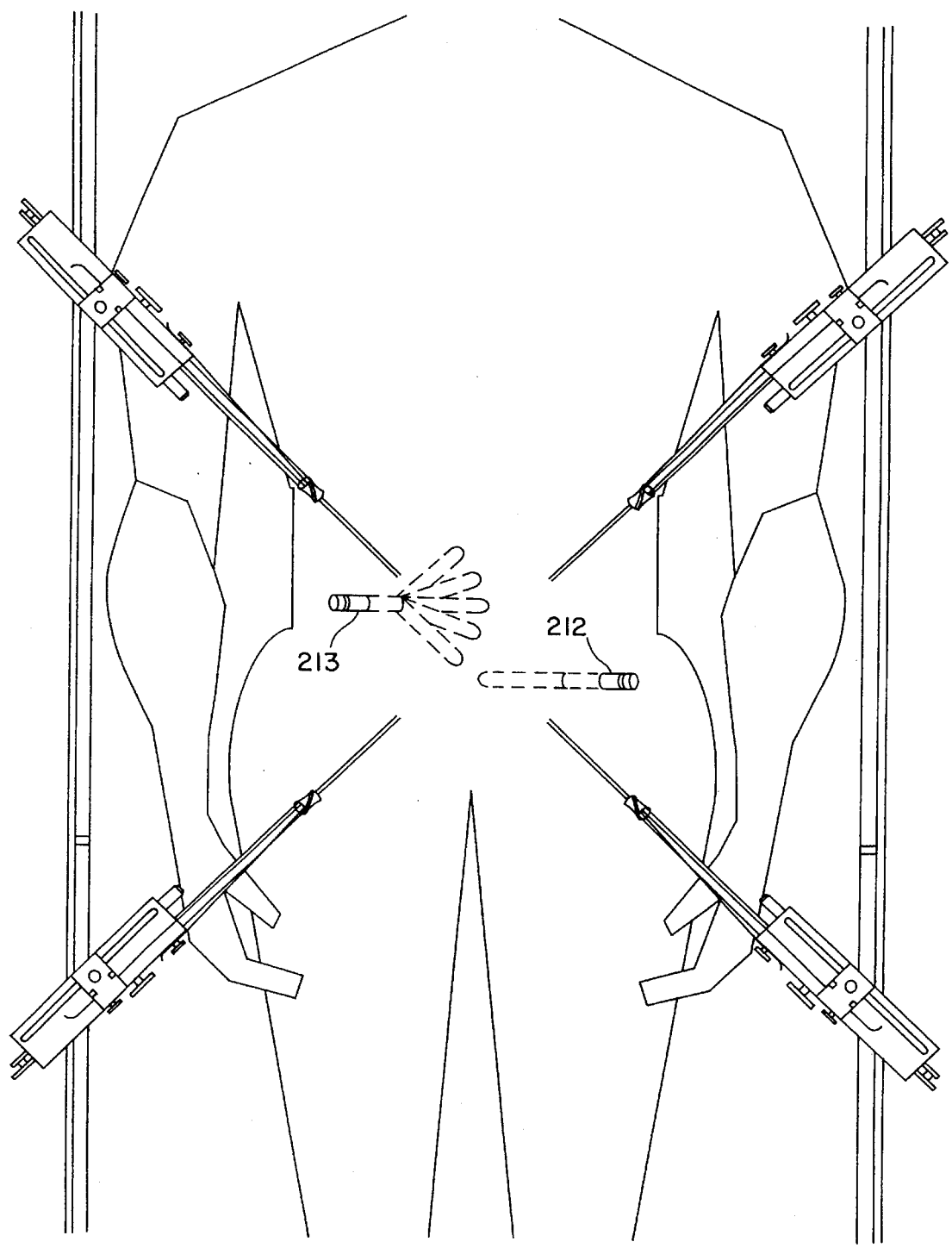

Trocars can then be used to create a hole through the muscular tissue into the abdominal cavity. The retractor may then be inserted into the opening, as shown as 212 in FIG. 11A, and then opened, as shown at 213 in FIG. 11A. Once in position, as shown at 214 in FIG. 11B, the retractor(s) can now move the superficial organs out of the way, as shown at 215 in FIG. 11B. The choice of manually or mechanically holding the retractor(s) in place is up to the surgeon. This procedure has enabled the surgeon to reach the posterior wall of the peritoneum.

It has thus been shown that there are provided devices, systems and methods which achieve the various objects of the invention and which are well adapted to meet the conditions of practical use.

The above description of the preferred embodiments is intended to be exemplary only, and not restricting the scope of the invention in any way, and should not be construed as providing the devices, systems and methods which must be utilized exclusively to practice the invention.

Many variations, modifications and changes in detail will be apparent to one skilled in the art and may be made in the devices, systems and methods of the present invention without departing from the spirit and scope thereof, and it is therefore to be understood that the invention is to be limited only by the scope of the appended claims.

What is claimed is:

1. A lateral suspension device comprising:

a wire guide for supporting a wire;

a horizontal arm for supporting said wire guide;

a pivot means for supporting said horizontal arm, said pivot means slidingly receiving said horizontal arm for movement relative thereto, said pivot means being rotatable about a horizontal axis;

firstlock means for releasably preventing sliding movement of said horizontal arm relative to said pivot means;

first clamp means, fixedly attached to said pivot means, for clampingly holding an end of a wire;

second clamp means, slidably attached to said pivot means for movement relative thereto, for clampingly holding an end of a wire;

gear means for moving said second clamp means relative to said pivot means;

second lock means, connected to said gear means, for locking said second clamp means in position relative to said pivot means;

vertical support means for supporting said pivot means above a surgical table;

third clamp means for releasably connecting said vertical support means to said surgical table.

* * * * *